United States Patent [19]
Lu et al.

[11] Patent Number: 5,783,702
[45] Date of Patent: Jul. 21, 1998

[54] PREPARATION OF CISAPRIDE

[75] Inventors: Yee-Fung Lu, Aurora; Clarke Slemon, Willowdale; Raymond So, Richmond Hill; Jan Oudenes, Thornhill; Teng-Ko Ngooi, Richmond Hill, all of Canada

[73] Assignee: Torcan Chemical Ltd., Aurora, Canada

[21] Appl. No.: 700,907

[22] Filed: Aug. 21, 1996

Related U.S. Application Data

[62] Division of Ser. No. 319,681, Oct. 7, 1994, Pat. No. 5,585,387.

[51] Int. Cl.$^6$ .................................................. C07D 211/74
[52] U.S. Cl. ........................................................ 546/220
[58] Field of Search ........................................... 546/220

[56] References Cited

U.S. PATENT DOCUMENTS

| | | | |
|---|---|---|---|
| 3,647,805 | 3/1972 | Ikikura et al. | 260/293.77 |
| 4,046,767 | 9/1977 | Cavella et al. | 546/197 |
| 4,069,331 | 1/1978 | Langbein et al. | 514/329 |
| 4,138,492 | 2/1979 | Noverola et al. | 514/316 |
| 4,745,192 | 5/1988 | Ertl | 546/19 |
| 4,962,115 | 10/1990 | Van Daele | 546/326 |

FOREIGN PATENT DOCUMENTS

| | | |
|---|---|---|
| 2002640 | 9/1988 | Spain |
| 2019011 | 5/1991 | Spain |
| 2019047 | 5/1991 | Spain |
| 2019234 | 6/1991 | Spain |
| 2019235 | 6/1991 | Spain |
| 2020128 | 7/1991 | Spain |
| 2053394 | 7/1994 | Spain |

OTHER PUBLICATIONS

Czarkie et al. "Tetrahedron", 1985 41(6) pp. 1049–1056.

G. Hofle, W. Steglich & H. Vorbruggen Angew. Chem. Int. Ed. Engl. 569–583 (1978) "4–Dialkylaminopyridines as Highly Active Acylation Catalysts".

H. Hiemstra & W. Nico Speckamp, Tet. Lett. vol. 24, 1407–1410 (1983) "Completely Regioselective α–acyliminium Ion Cyclizations with Allyl and Propargyl Silanes".

C.A. Grob & C. Wagner, Hel. Chi. Acta. 1699–1707 (1955) "Die Konkurrierende 1,2–und 1,3–acylwanderung".

G. Fodor & J. Kiss, JACS vol. 72, 3495–3497 (1950) "Acyl Migration O–N in the Diastereomeric 2–aminocyclohexyl Benzoate".

J.H. Dodd et al., Syn. Comm., vol. 23, 1003–1008 (1993) "A Mild, Nonacidic Method for the Conversion of Carboxylic Esters into Oxazolines".

R.O. Hutchins et al., J.O.C., vol. 48, 3 412–3422 (1983) "Stereoselective Reductions of Substituted Cyclohexyl and Cyclopentyl . . . ".

H.C. Brown & S. Krishnmaurthy, Tetrahedron, vol. 35, 567–607 (1979) "Tetrahedron Report Number 64" Forty Years of Hydride Reductions.

G.E. McCasland & Donald A. Smith, "Stereochemistry of Aminocyclonols Synthesis of cis Epimers via Oxazolines The Aminocyclopentanols" J. Am. Chem. Soc. 72, 2190 (1950).

Herbert O. House & Forrest A. Richey, Jr., "Use of Ketoximes Derivatives to Prepare α–Acetoxyketones", Journal of Organic Chemistry 34, 1430 (1969).

*Primary Examiner*—C. Warren Ivy
*Assistant Examiner*—Garth M. Dahlen
*Attorney, Agent, or Firm*—Ridout & Maybee

[57] ABSTRACT

Cisapride, i.e. cis-4-amino-5-chloro-N-[1-[3-(4 fluorophenoxy)propyl]-3-methoxy-4-piperidinyl]-2-methoxybenzamide, and similar benzamide derivatives, are prepared from novel 1-aryloxyalkyl- or 1-aralkyl-3-arylcarbonyloxy-4-oxo-piperidines, by nuclear substituent re arrangement involving acyl transfer under animal forming conditions, to give the corresponding 1-aryloxyalkyl- or 1-aralkyl-3-hydroxy-4-lower alkoxy-4-arylamido piperidine. This in turn is readily converted to the corresponding 3-oxo-4-arylamido-piperidine by reaction with strong organic acid, which can then be reduced, deprotected and 3-methylated to give the final compound, e.g. cisapride.

5 Claims, 1 Drawing Sheet

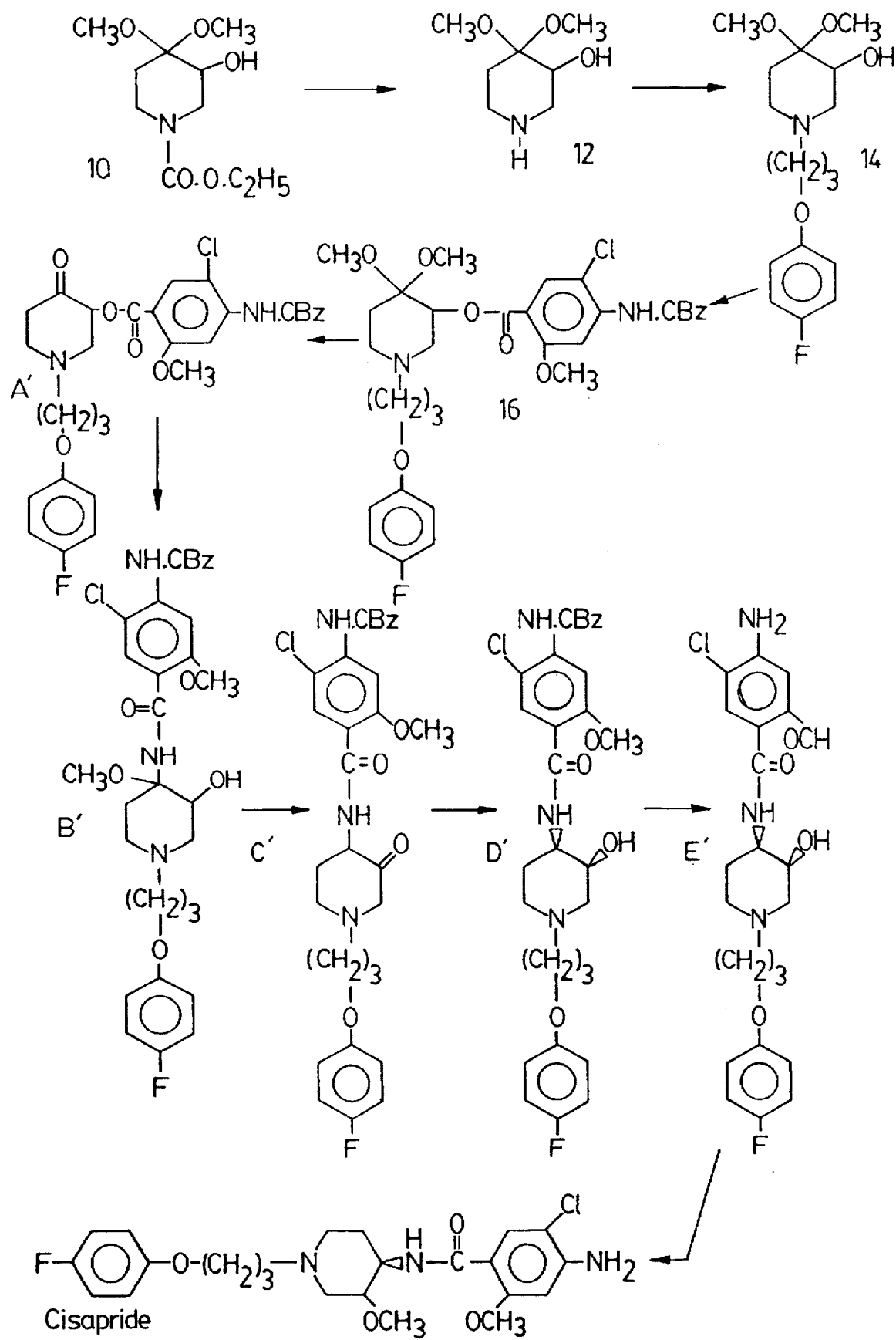

PREPARATION OF CISAPRIDE

This is a division of application Ser. No. 08/319,681, filed Oct. 7, 1994, now U.S. Pat. No. 5,585,387.

FIELD OF THE INVENTION

This invention relates to synthesis of pharmaceutically active compounds, and to intermediates for use in such synthesis. From a more specific aspect, it relates to methods for making the pharmaceutical cisapride, intermediates useful in such a synthesis and methods for making such intermediates.

BACKGROUND OF THE INVENTION AND PRIOR ART

Cisapride, the full chemical name of which is cis-4-amino-5-chloro-N-[1-[3-(4-fluorophenoxy)propyl]-3-methoxy-4-piperidinyl]-2-methoxy-benzamide, and the chemical structural formula of which is:

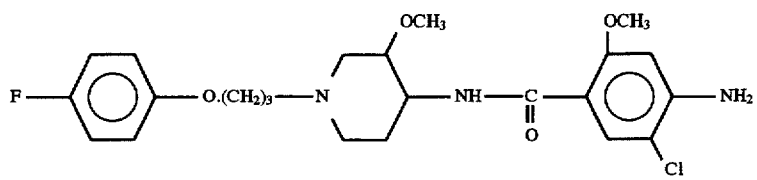

is a known compound, the preparation and properties of which are described in Canadian Patent 1,183,847 Van Daele, issued Mar. 12, 1985. It is also the subject of Entry No. 2318 of The Merck Index, 11th Edition. According to the disclosure of Canadian Patent 1,183,847, it has pharmacological properties as a stimulator of motility of the gastrointestinal system, rendering it useful as a peristaltic stimulant in the treatment of disorders associated with the gastrointestinal tract.

Three basic methods for the chemical synthesis of cisapride and related benzamide derivative compounds are described, in greater or lesser detail, in aforementioned Canadian patent 1,183,847. In general terms, these three methods are:

in the first method, reaction of an appropriately substituted piperidine-amine with an appropriately substituted benzoic acid or functional equivalent thereof, to form the amide linkage, thus:

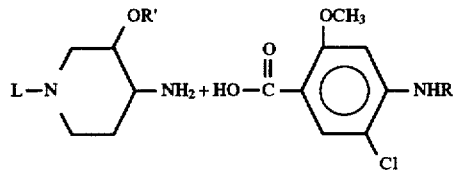

in the second method, reaction of a 7-oxo-3-azabicyclo[4.1.0]-heptane with an appropriately substituted benzamide, followed by O-alkylation of the piperidine ring, thus:

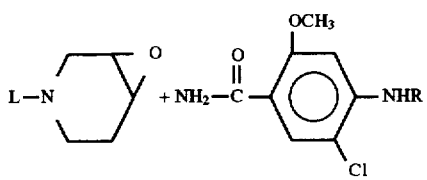

in the third method, reductive N-alkylation of an appropriate piperidinone with an appropriately substituted benzamide, thus:

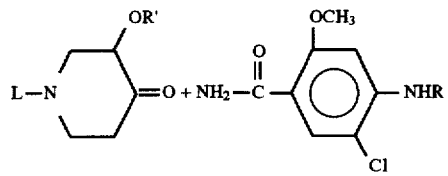

In all of these general formulae, L, R' and R each represent one of a wide variety of radicals according to the patent, but in the specific case of cisapride preparation, they represent respectively 3-(4-fluorophenoxy) propyl methyl and hydrogen or an amino protectant group.

Other syntheses involving the conversion of one member of the class of benzamide derivatives of Canadian patent 1,183,847 to another member of the same class and syntheses for compounds of the class having groupings different from those of cisapride, are also disclosed in the aforesaid Canadian patent.

These prior art syntheses for cisapride all involve the formation of an amide bond between the piperidine moiety and the benzoic acid derived moiety, with the appropriate substituents on each moiety already in place. The first of these methods is disadvantageous because the 4-aminopiperidine starting material must be produced by a reductive amination which produces a mixture of cis with some trans stereoisomer. Since only the cis isomer is pharmaceutically important, in the pharmaceutically important case of cisapride, the cis isomer must at some stage be separated from the cis-trans mixture. This is inefficient and wasteful of material since several recrystallizations may be required. The second of these methods results in substantial amounts of trans isomer, which is not useful in producing such materials such as cisapride. The third method is not fully detailed in the patent disclosure, and turns out to be impractical on a larger scale.

SUMMARY OF THE INVENTION

It is an object of the present invention to provide a novel process for preparing cisapride and similar benzamide derivatives, highly stereoselectively and in a predominantly cis configuration.

It is a further object to provide novel chemical compounds useful as intermediates in such preparation.

From a first aspect, the present invention provides novel substituted 4-oxo-piperidine compounds, namely 1-aryloxyalkyl- or 1-aralkyl-3-arylcarbonyloxy-4-oxo-piperidines of the general formula A given below:

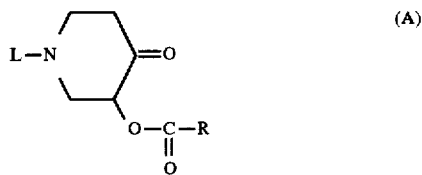

which are convertible to novel 1-aryloxyalkyl- or 1-aralkyl-3-hydroxy-4-lower alkoxy-4-arylamido piperidines of the general formula B given below:

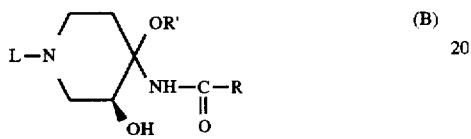

The process of converting compounds of formula A into compounds of formula B, which constitutes another aspect of the present invention, is a novel and totally surprising nuclear substituent rearrangement involving acyl transfer under aminal forming conditions.

Piperidines of general formula B, it has been found, can be readily converted to the corresponding 3-oxo-4-arylamido compounds of general formula C:

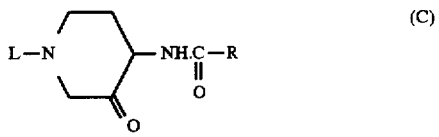

by reaction with strong organic acid, for example trihaloacetic acid, methanesulfonic acid, trifluoromethane sulfonic acid and the like.

In the above general formulae A, B and C, L in each case represents aralkyl or aryloxyalkyl in which the alkyl portion has from 1 to 6 carbon atoms and the aryl nucleus is optionally substituted with up to 3 substituents independently selected from halo, lower alkyl and lower alkoxy, or alkyl having from 1 to 6 carbon atoms; R' represents alkyl of from 1 to 6 carbon atoms, or benzyl; and R represents a phenyl group optionally substituted with up to 3 substituents independently selected from halo, amino, protected amino, alkyl of 1 to 6 carbon atoms, and alkoxy of 1 to 6 carbon atoms.

The success of the reaction to convert the 3-hydroxy-piperidine compounds to the corresponding 3-oxo piperidine compounds, i.e. compound B to compound C, is most surprising, since the scientific literature rarely describes compounds with the 3-oxo piperidine sub-structure, and where they appear they are indicated to be quite unstable. Their formation as a stable intermediate for subsequent utilization in an organic chemical synthesis process is accordingly contra-indicated. However, it has now been found that this instability is not manifested, at least under the strongly acidic conditions employed in the processes of the present invention. Once compound C has been formed, its subsequent reduction to the corresponding 3-hydroxy compound, deprotection and methylation at the 3-position of the piperidine ring to form compounds such as cisapride is relatively straightforward, and in fact significantly advantageous. The step of hydride reduction of the oxo group to form a hydroxyl group can be conducted stereo specifically to form an intermediate in which the 3-hydroxyl group and the 4-amido group on the piperidine nucleus are disposed in the cis relationship to one another, as required in cisapride, with no formation of contaminant trans isomer. Deprotection is routine.

A further aspect of the invention relates to the discovery of a special method for the selective methylation of the 3-hydroxyl group.

BRIEF REFERENCE TO THE DRAWINGS

The single FIGURE of accompanying drawings illustrates the most preferred synthetic process according to the invention, namely that specifically applied to the synthesis of cisapride.

DESCRIPTION OF THE PREFERRED EMBODIMENTS

Preferred compounds of formula A according to the present invention are those in which L represents (halo-substituted phenyl) oxypropyl, especially 4-fluorophenyl-oxypropyl, and in which R represents a substituted phenyl group, especially 2-methoxy-4-amino-5-chlorophenyl and N-protected versions thereof such as carbobenzoxy-protected versions thereof. The especially preferred compound A, the structural formula of which is shown and labelled "A" on the FIGURE of drawings, is specifically useful in cisapride synthesis.

Compound A itself can be prepared by a reaction sequence which starts from ethyl 4,4-dimethoxy-3-hydroxy-1-piperidine carboxylate, a known compound (see European patent 76530 Janssen, or European patent 121,972 Janssen, priority date Oct. 17, 1984). As shown diagrammatically on the FIGURE, this compound 10 is decarboxylated e.g. by alkaline hydrolysis, to form the corresponding piperidine compound 12 with free secondary amine group at position 1. This is reacted with 1-chloro-3-(4-fluorophenoxy)propane under basic conditions, to form compound 14 as shown on the FIGURE. Reaction of compound 14 with 2-methoxy-4-carbobenzoxyamino-5-chloro-benzoic acid (or acyl halide thereof) forms compound 16 shown on the FIGURE. Conversion of compound 16 to the especially preferred embodiment of compound A according to the invention may be accomplished by acid hydrolysis using a strong mineral acid such as sulphuric acid, in a solvent such as methylene chloride.

The reaction of compound A to form compound B is one of nuclear substituent rearrangement, and is a reaction for which no similar precedent is known to exist. Important preconditions for it appear to be the piperidine ring substituted by oxo at the 4-position and —O—CO-aryl at either the 3-position or the 5-position, the presence of ammonium carboxylate, a carboxylic acid and the use of a nucleophilic alcoholic solvent. The reaction mechanism, although not fully elucidated and not to be construed as binding or in any way limiting on the scope of the present invention, is believed to involve an initial attack by the ammonia supplied from the ammonium carboxylate on the hemiketal formed by the reaction of the ketone with the solvent alcohol, accompanied by transacylation of the transiently formed aminal by the proximate ester at the 3 or 5 position. The result is the insertion of an alkoxy substituent as well as an amide substituent at position 4 of the piperidine. At the same time the oxygen group left at position 3 becomes protonated to form a hydroxyl group at that position, giving the compound B as shown on the FIGURE.

The conversion of compound B to compound C takes place by reaction with strictly anhydrous solutions of strong organic acids, for example trichloroacetic acid, trifluoroacetic acid, trifluoromethanesulfonic acid or methanesulfonic acid. The use of strongly acidic conditions for conducting this reaction appears to be essential. The resulting product compound C is a 3-oxo-piperidine, a class of compounds which are rarely reported because they are apparently unstable under most conditions used to generate them. The formation and isolation of such an intermediate would not therefore be expected to occur to yield a useful amount of product. According to the process of this invention, however, the reaction not only occurs, but proceeds under mild conditions to give high (over 80%) yield of product C, which can be isolated as a solid. The use of the strongly acidic conditions may be the key to the successful preparation of the product. At the same time as the conversion of the 3-hydroxyl group to a 3-oxo group, the alkoxy (normally methoxy) group is removed from the 4-position of the piperidine ring. With the discovery of the surprisingly facile and efficient route from A to B to the surprisingly stable product C, a new area of chemical synthetic routes to cisapride and similar benzamide derivatives of pharmaceutical and scientific interest is opened up.

The next step in the synthesis according to the invention, as applied in its most preferred embodiment to the manufacture of cisapride, is the conversion of the 3-oxo compound C to the corresponding 3-hydroxy compound D. The problem of stereoselectively reducing cyclic ketones to alcohols is well known in the art. This is done by selection of an appropriately bulky hydride donor selected from such common reagents such as lithium aluminum hydride, lithium trialkoxyaluminum hydrides, lithium n- or t-butyldiisobutylaluminum hydride, sodium bis(2-methoxyethoxy)aluminum hydride, tetramethylammonium borohydride, 9-borabicyclo[3,3,1] nonane ate complexes, calcium borohydride, chlorobis(cyclopentadienyl)-tetraboratozirconium (IV), lithium borohydride, lithium cyanoborohydride, lithium 9,9-dibutyl-9-borabicyclo[3,3,1] nonane, lithium dimesitylborohydride bisdimethoxymethane, lithiumperhydro-9b-boraphenalylhydride, lithiumtri-sec-butyl borohydride, lithiumtriethyl-borohydride, lithium tris-i-amyl borohydride, potassium 9-(2,3-dimethyl-2-butoxy)-9-boratobicyclo[3,3,1]nonane, potassium tri-sec-butylborohydride, potassium triisopropoxyborohydride, sodium acetanilidoborohydride, sodium borohydride, sodium cyanoborohydride, sodium triacetoxyborohydride, sodium trimethoxyborohydride, tetrabutylammonium borohydride, tetrabutylammonium cyanoborohydride, tetrabutylammonium octahydrotriborate, tetramethylammonium borohydride or zinc borohydride. Alternatively, the reduction can be performed using an appropriately bulky hydrogen donor such as borane-alkylamines, dicyclohexylborane, diisocamphylborane, diisoamyl borane or t-hexylborane. Potassium tri-sec-butylborohydride (potassium selectide) is a preferred reagent. The reaction takes place substantially quantitatively and stereoselectively, to produce compounds in which the amide group at position 4 of the piperidine ring and the hydroxyl group at position 3 of the piperidine ring are disposed cis to one another, the disposition required in the end-product cisapride.

The protecting group is removed from the amino group at position 4 of the tri-substituted benzene ring, by methods well known in the art. A particularly suitable method is hydrogenation, e.g. using hydrogen gas over a palladium catalyst. This process yields compound E shown on the FIGURE, which is convertible to cisapride as the final step in the overall synthetic process.

A particularly advantageous way of conducting this final conversion, and one which forms a specific preferred embodiment of the present invention, involves the reaction of one equivalent of compound E with two equivalents of sodium hydride followed by quenching with 1 equivalent of dimethylsulfate. This reaction is best conducted in tetrahydrofuran or similar solvent, and at temperatures from about $-30°$ to $0°$ C. Selective methylation of the 3-hydroxy group occurs under such conditions.

SPECIFIC DESCRIPTION OF THE MOST PREFERRED EMBODIMENTS

The invention will be further described for illustrative purposes, by reference to the following specific working, non-limiting examples.

EXAMPLE 1

This example illustrates the conversion of compound 10 to compound 12, on the accompanying FIGURE.

55 g of 1-ethoxycarbonyl-4,4-dimethyl-3-hydroxypiperidine, compound 10, was dissolved in 550 ml isopropanol, then 56 g of potassium hydroxide was added. The reaction mixture was heated to reflux for 7 hours.

The product mixture was filtered, and the product was rinsed with isopropanol. It was concentrated using a rotovap, and 500 ml methylene chloride was added to dissolve it. Then it was washed twice, with 100 ml portions of water, the aqueous layers were back extracted with 3×150 ml methylene chloride, and all the organic layers combined. This organic phase was dried using magnesium sulphate, concentrated using a rotovap and vacuum for ½ hour. The product, 3-hydroxy-4,4-dimethoxy-piperidine, compound 12, was obtained as an oil, in a yield of 19 gm.

EXAMPLE 2

This example illustrates the preparation of compound 14 on the accompanying FIGURE, 4,4-dimethoxy-1-[3-(fluorophenoxy)propyl]-3-hydroxypiperidine, from compound 12 prepared according to Example 1 above.

This procedure was conducted in a 2 L 3-necked flask with a condenser and a nitrogen bubbler and stirrer. The reaction was conducted under an atmosphere of nitrogen.

To the flask was added 200 ml methyl isobutyl ketone (MIBK), 74.6 gm potassium carbonate, followed by 67.8 gm of 1-chloro-3-(4-fluorophenoxy)propane in a further 100 ml MIBK. Then 72.5 gm of the starting material, compound 12, in an additional 400 ml MIBK was added, followed by sodium iodide catalyst (0.6 gm).

The reaction took place under reflux overnight, then an additional 28 gm of potassium carbonate was added and the refluxing was continued for a further 5 hours.

The reaction mixture was then cooled to room temperature, the solid was filtered off and washed with 200 ml of MIBK. The organic layers were combined and concentrated on a rotary evaporator, to yield 110 gm of a brownish solid. Five hundred and fifty (550) mL of hexane was added and the solid triturated overnight. The light brown solid was filtered and washed with 100 mL of hexane, and dried in vacuum at 50° C. to give 70 grams of compound 14.

EXAMPLE 3

This example illustrates the preparation of compound 16 on the accompanying FIGURE, 1-(4-fluorophenyl) oxypropyl-4,4-dimethoxy-3-(2-methoxy-4-carbobenzoxyamino-5-chlorobenzyloxy)piperidine, from compound 14 prepared as described in Example 2.

To a flame dried flask under a nitrogen atmosphere, there was added 400 ml of methylene chloride, 15.6 gm of compound 14 followed by 6.7 gm of 4-dimethylaminopyridine (DMAP). This mixture was stirred at room temperature for 5 minutes, and then there was added 17.71 gm of (2-methoxy-3-carbobenzoxyamino-4-chlorobenzoyl chloride. The reaction mixture was stirred at room temperature overnight. A chromatographic check indicated a certain amount of starting material 14 still remaining, and so another 0.3 equivalent (5.3 gm) of the benzoyl chloride was added. The reaction mixture was stirred at room temperature for sixty-four hours, quenched with 500 ml water, the methylene chloride fraction was separated, and the aqueous layer was extracted with 200 ml methylene chloride, twice. The methylene chloride extracts were combined and washed with brine (200 ml), separated, and the aqueous phase backwashed with 100 ml methylene chloride.

The combined methylene chloride fractions were dried over magnesium sulfate, and the solid filtered off after 5 minutes. The organic phase was concentrated under aspirator pressure, to give a dark brownish oil. The crude product was subjected to purification on a silica gel column, eluted with hexane:ethylacetate mixtures, and the fractions containing the product were concentrated under reduced pressure. An 85% (27 gm) yield of the product 16 was obtained.

NMR spectra data confirming the structure of compound 16:

H NMR (CDCl, 300 MH) (ppm):1.80–2.15(m,5H), 2.26 (brt, 1H, J=15 Hz), 2.40–2.70 (m, 3H), 2.78 (brd, 1H, J=15 Hz), 3.10 (brd, 1H, J=15 Hz), 3.20 (S,3H), 3.28 (S,3H), 3.95 (brS, 5H), 5.14 (brS, 1H), 5.28(S,2H), 6.70–6.78 (m,2H), 6.86–6.96 (m,2H), 7.38–7.50 (m, 5H), 7.90 (S,1H), 8.05 (S,1H).

C NMR(CDCl, 75 MH, (ppm): 26.83, 28.78,47.48,48.02, 49.76, 53.42, 53.84, 56.28, 66.53, 67.71, 69.04, 98.09, 102.66, 112.06, 114.22, 115.23, 115.33, 115.72, 128.49, 128.69, 128.73, 132.32, 135.30, 139.35, 152.61, 154.97, 155.30, 158.45, 159.87, 163.19.

EXAMPLE 4

In this example, compound A' shown on the attached FIGURE, 1-(4-fluorophenyl)oxypropyl-4-oxo-3-[(2-methoxy-4-carbobenzoxyamino-5-chlorobenzoyloxy] piperidine was prepared from compound 16 made according to Example 3.

5.50 gm of compound 16 from Example 3 was dissolved in 5 ml of methylene chloride and cooled to 0° C. 20 ml of 50% sulphuric acid was added, and the mixture removed from an ice bath and warmed to room temperature over 1 hour. Then there was slowly added over a period of 1½ hours 5 ml of concentrated sulphuric acid, in three intermittent additions, with stirring, at room temperature. The mixture was then transferred into an ice bath, basified with 25% sodium hydroxide solution, with the temperature being kept below 10° C. The product mixture was extracted with 2 aliquots of 200 ml methylene chloride, the methylene chloride extracts were washed with brine, separated and dried over magnesium sulfate. There was obtained 4.8 gm of crude material, in the form of a viscous yellowish semi-solid.

The product was precipitated by addition of methylene chloride (1 ml) and methanol (10 ml) and stirred to form a white precipitate. The solid which was filtered off was washed with 1 ml of methylene chloride, dried in an oven at 40° C. to give 2.2 gm (43%) of white solid.

Spectral data confirming the structure of compound A':

H NMR (CDCl, 300 MHz) (ppm): 1.60–1.80 (brS, 1H), 2.00–2.12 (m,2H), 2.40–2.60 (m,3H), 2.70–2.90 (m,3H), 3.14–3.27 (m,1H), 3.42–3.51 (m,1H),3.92 (S,3H), 4.03 (t,2H,J=7 Hz), 5.25 (s,2H), 5.52 (dd,1H,J=7.5,11.5 Hz), 6.80–6.88 (m,2H), 6.93–7.02 (m,2H), 7.35–7.56 (m,5H), 7.95 (s,1H), 8.05 (s,1H).

C NMR (CDCl, 75 Mz) (ppm): 27.18, 39.88, 53.15, 56.22, 57.09, 66.15, 67.56, 73.76, 102.62,112.03, 113.27, 115.25, 115.35, 115.51, 115.82, 128.35, 128.55, 128.60, 132.26, 135.20, 139.49, 152.48, 154.92, 155.51, 158.66, 159.78, 162.43, 202.39.

EXAMPLE 5

In this example, the product A' obtained according Example 4 was subjected to acylating nuclear rearrangement, to prepare compound B' shown on the attached FIGURE, 1-(4-fluorophenyl) oxypropyl-3-hydroxy-4-[[2-methoxy-4-carbobenzoxyamino-5 -chlorobenzoyl]amino]-piperidine.

To a flask containing 2.10 gm of starting material compound A there was added 50 ml of methanol to obtain a white suspension. To this was added 5.2 gm of ammonium acetate and 2 ml of acetic acid, and the mixture stirred at room temperature overnight. Then most of the solvent was evaporated off, under reduced pressure, 50 ml of methylene chloride was added, and the mixture was basified with 4% sodium hydroxide until pH 10 was achieved. The product was extracted with 2 aliquots of methylene chloride, then all the methylene chloride extracts were combined and washed with brine. The organic layer was separated and dried over magnesium sulfate, and the filtrate liquid was concentrated under a high vacuum pump to give a yellowish oil product, weight 2.01 gm, compound B' (which was predominantly a single stereoisomer by NMR).

Spectral data confirming the structure of compound B':

H NMR (CDCl, 300 MHz) (ppm): 1.30 (brs, 1H), 1.40–1.80 (m, 1H), 1.90–2.20 (m,4H), 2.30–3.0 (m,6H), 3.38 (s,3H), 3.90–4.05 (m,6H), 5.24(s,2H),6.75–6.85 (m,2H), 6.90–7.05 (m,2H), 7.32–7.52 (m,5H), 8.06 (s,1H), 8.18 (s,1H), 8.28 (s,1H).

C NMR (CDCl, 75 MHz) (ppm): 26.93, 30.23, 49.86, 50.03, 54.29, 55.48, 56.46, 66.72, 67.66, 70.58, 85.56, 102.44, 113.59, 115.39, 115.50, 115.57, 115.88, 117.23, 128.4, 128.67, 128.72, 132.36, 135.34, 138.39, 152.74, 155.08, 155.62, 157.03, 158.77, 164.05.

EXAMPLE 6

This example illustrates the conversion of compound B', prepared according to Example 5 above, into the corresponding 3-keto compound, namely 1-[3-(4-fluorophenoxy] propyl]-3-oxo-4-[[(2-methoxy-4-carbobenzoxyamino-5-chlorobenzoyl]amino]-piperidine, compound C' on the attached FIGURE.

To a flame dried flask with molecular sieves, under a nitrogen atmosphere, there was added 1.472 gm of starting material compound B, along with 50 ml of methylene chloride. The mixture was cooled to 0° C. and 1.13 ml of trifluoroacetic acid was added dropwise. The mixture was slowly warmed to room temperature overnight, and then 20 ml of 4% sodium hydroxide was slowly added. The mixture was extracted with 3 50 ml aliquots of methylene chloride, the organic extracts were combined, and washed with 50 ml of brine. The organic layer was separated and dried over magnesium sulfate. After 5 minutes, the solid was filtered off, and the mother liquid was concentrated under aspirator pressure and pumped under vacuum. There was obtained 1.133 (81% yield) of a yellowish solid, compound C'.

Spectral data confirming the structure of compound C' so prepared:

H NMR (CDCl, 300 MHz) (ppm): 1.60–1.88 (m, 1H), 1.90–2.05 (m, 2H), 2.60–2.90 (m, 4H), 2.95 (brd, 1H, J=12 Hz), 3.05 (brd, iH, J=15 Hz), 3.42 (brd, 1H, J=12 Hz), 4.00 (t, 2H, J=7Hz), 4.04 (s,3H), 4.10–4.18 (m, 1H), 4.62–4.75 (m, 1H), 5.26 (s, 2H), 6.78–6.84 (m,2H), 6.92–7.00 (m,2H), 7.38–7.52 (m,5H), 8.10 (s, 1H), 8.18 (s, 1H), 8.78 (d, 1H, J=7 Hz).

C NMR (CDCl, 75 MHz) (ppm): 26.86, 32.54, 51.40, 54.39, 56.47, 57.35, 63.55, 66.27, 67.66, 102.37, 113.68, 115.38, 115.49, 115.62, 115.92, 116.35, 128.45, 128.68, 128.74, 132.15, 135.36, 138.37, 152.74, 155.02, 155.65, 157.33, 158.81, 163.51, 202.69.

EXAMPLE 7

This example illustrates the conversion of compound C' prepared according to Example 6, to compound D' shown on the attached FIGURE, namely cis-1- [3-(4-fluorophenoxy] propyl-3-hydroxy-4-[(2-methoxy-4-carbobenzoxyamino-5-chlorobenzoyl]amino] piperidine.

To a flame dried flask under nitrogen atmosphere there was added and dissolved 5.41 gm of the starting material compound C' in 100 ml of tetrahydrofuran. The solution was cooled to −30° C., and then potassium selectide (10.4 ml of a 1M solution in THF) was added dropwise. The mixture was stirred at −30° C. for 1 hour, whereupon it was quenched with 200 ml of 4% sodium hydroxide and 20 ml water. The mixture was warmed to room temperature, extracted with 2 portions of 50 ml ethyl acetate, and the organic extracts were combined. The organic phase was washed with 50 ml brine, separated, collected and dried over magnesium sulfate. The solid was filtered off, and the mother liquid was concentrated under reduced pressure, to obtain a yellowish oil. The crude product was purified using a silica gel column, eluting with 200 ml ethyl acetate then with 600 ml 10% methanol in ethyl acetate. Fractions containing the were collected, and concentrated to obtain a yellowish solid, weight 3.81 gm, compound D'.

Spectral data confirming the structure of compound D' so prepared:

H NMR (CDCL, 300 MHz) (ppm): 1.48–1.72 (m, 1H), 1.80–1.98 (m,aH), 2.10 (brt, 1H, J=15 Hz), 2.26 (brd, 1H, J=15 Hz), 2.40–2.60 (m,2H), 2.80 (brd, 1H, J=15 Hz), 2.95 (brd, 2H, J=15 Hz), 3.80 (brs, 1H), 3.92 (s, 3H), 3.93–4.05 (m,3H), 5.18 (s, 2H), 6.70–6.80 (m, 2H), 6.90–7.00 (m,2H), 7.28–7.45 (m, 5H), 7.98 (s, 1H), 8.14 (s, 1H), 8.22 (d, 1H, J=7 Hz).

C NMR (CDCl, 75 MHz) (ppm): 26.80, 27.08, 48.48, 51.90, 54.29, 56.27, 58.39, 66.46, 67.33, 67.47, 102.23, 113.51, 115.23, 115.33, 115.50, 115.80, 118.75, 128.30, 128.51, 128.59, 132.01, 135.26, 137.91, 152.62, 154.91, 155.49, 156.93, 158.64, 163.02.

EXAMPLE 8

Compound D' prepared as described in Example 7 was deprotected to yield compound E' as shown on the attached FIGURE, namely cis-4-amino-5-chloro-N-[1-[3-(4-fluorophenoxy)propyl]-3-hydroxy-4-piperidinyl]-2-methoxy-benzamide.

0.41 gm of the starting material compound D from Example 7 was dissolved in 30 ml acetic acid, transferred into a hydrogenation flask, and 0.1 gm of 5% palladium on carbon black, 50% water of hydration was added. The flask was connected to the hydrogenation equipment and flashed with hydrogen 3 times at 15 psi, the reaction being left to proceed for ½ an hour. The hydrogenation was stopped, the product filtered off the catalyst and washed with methanol. The product slowly was concentrated, and to it was added 10 ml methylene chloride and 4% sodium hydroxide to basify it. It was extracted with 2 aliquots of 10 ml methylene chloride. All of the organic extracts were combined, washed with brine, separated and the organic phase dried over magnesium sulfate. The solid was filtered off. The mother liquid was concentrated under aspirator pressure, to give a slightly yellow solid, of weight 0.33 gm. The crude was subjected under vacuum pump for 5 hours, to obtain a final yield of 0.30 gm, 92%, compound E'.

Spectral data confirming the structure of compound E' so prepared:

H NMR (CDCl, 300 MHz) (ppm): 1.60–1.80 (m, 1H), 1.90–2.02 (m, 3H), 2.20 (brt, 1H, J=15 Hz), 2.32 (brd, 1H, J=15 Hz), 2.45–2.60 (m,2H), 2.80–3.10 (m, 3H), 3.84 (brs, 1H), 3.90 (s, 3H), 4.00 (t, 2H,J=7 Hz), 4.10–4.20 (m,1H), 4.38 (s,2H), 6.28 (s, 1H), 6.75–6.85 (m,2H), 6.90–7.05 (m, 2H), 8.10 (s, 1H), 8.18 (d, 1H, J=7 Hz).

C NMR (CDCl, 75 MHz) (ppm): 26.82, 27.20, 49.29, 51.89, 54.26, 55.96, 58.40, 66.48, 67.53, 97.73, 111.26, 112.34, 115.23, 115.33, 115.48, 115.79, 132.78, 146.63, 154.93, 155.47, 158.62, 163.81.

EXAMPLE 9

Compound E' prepared according to Example 8 above was converted to cisapride.

To a 200 ml 3 neck round bottom flask under nitrogen atmosphere there was added 0.975 gm (0.024M) of sodium hydride in 100 ml of dried tetrahydrofuran, 5 gm (0.011M) of compound E' from Example 8 dissolved in 50 ml of tetrahydrofuran, and the mixture was stirred at room temperature for about 30 minutes, then cooled to about −25° C. 1.10 ml of dimethyl sulfate was added, and the temperature was kept between −20° and −25° C. whilst the reaction proceeded. The product was worked up by adding isopropanol to the reaction mixture, concentrating the entire mixture under the rotovap, to cause some solid precipitation. A mixture of 1:1 isopropanol:water was added, and the mixture stirred at room temperature for 2 hours. The solid was filtered off, washed with isopropanol, dried at 40°C. in a vacuum oven. A yield of 68% of cisapride was obtained.

Spectral data confirming the structure of cisapride so formed:

H NMR (CDCl, 300 MHz) (ppm): 1.40–1.80 (brs, 1H), 1.87–2.10 (m,4H), 2.20–2.36 (m,2H), 2.44–2.60 (m,2H), 2.74–2.84 (m,1H), 3.00–3.14 (m,1H), 3.45 )s,3H), 3.92 (s, 3H), 4.00 (t, 2H, J=7 Hz), 4.10–4.30 (m,1H), 4.40 (brs, 2H), 6.32 (s,1H), 6.80–6.90 (m,2H), 6.95–7.10 (m,2H), 8.12 (s,1H), 8.20 (d, 1H, J=7 Hz).

C NMr (CDCl, 75 MHz) (ppm): 26.71, 27.67, 47.98, 51.67, 53.49, 54.96, 55.83, 56.77, 66.84, 76.49, 97.85, 111.41, 112.60, 115.33, 115.41, 115.71, 132.80, 146.57, 154.97, 155.48, 157.47, 158.63, 163.64.

What is claimed is:

1. 1-Aryloxyalkyl- or 1-aralkyl-3-arylcarbonyloxy-4-oxo-piperidines of the general formula A:

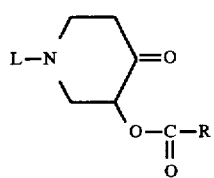

(A)

in which L represents aralkyl or aryloxyalkyl in which the alkyl portion has from 1 to 6 carbon atoms and the aryl nucleus is optionally substituted with up to 3 substituents independently selected from halo, lower alkyl and lower alkoxy, or alkyl having from 1 to 6 carbon atoms; and R represents a phenyl group optionally substituted with up to three substituents independently selected from halo, amino, protected amino, alkyl of from 1 to 6 carbon atoms, and alkoxy of from 1 to 6 carbon atoms.

2. 4-Oxo-piperidines as claimed in claim 1 wherein L represents 3-[(4-fluorophenoxy)propyl].

3. 4-Oxo-piperidines as claimed in claim 2 wherein R represents 2-methoxy-4-(protected-amino)-5-chlorophenyl.

4. 4-Oxo-piperidines as claimed in claim 1 wherein R represents 2-methoxy-4-amino-5-chlorophenyl.

5. 4-Oxo-piperidines as claimed in claim 3 wherein R represents 2-methoxy-4-carbobenzoxyamino-5-chlorophenyl.

* * * * *